United States Patent [19]
Buenter

[11] Patent Number: 5,880,107
[45] Date of Patent: Mar. 9, 1999

[54] SODIUM HYALURONATE BASED OPHTHALMIC FORMULATION FOR USE IN EYE SURGERY

[75] Inventor: René-Pierre Buenter, Venthone, Switzerland

[73] Assignee: Chemedica S.A., Vouvry, Switzerland

[21] Appl. No.: 770,331

[22] Filed: Dec. 20, 1996

[30] Foreign Application Priority Data

Dec. 22, 1995 [IT] Italy .................... MI95A2744

[51] Int. Cl.$^6$ .................... A61K 31/715; A61K 31/34
[52] U.S. Cl. .................... 514/54; 514/78.04; 514/474; 514/912
[58] Field of Search .................... 514/78.04, 54, 514/474, 912

[56] References Cited

U.S. PATENT DOCUMENTS

| | | |
|---|---|---|
| 4,141,973 | 2/1979 | Balazs . |
| 4,886,786 | 12/1989 | Lindstrom et al. . |
| 4,920,104 | 4/1990 | Devore et al. . |
| 5,409,904 | 4/1995 | Hecht et al. . |
| 5,614,506 | 3/1997 | Falk et al. .................... 514/54 |

FOREIGN PATENT DOCUMENTS

| | | |
|---|---|---|
| 0 464 727 A2 | 6/1991 | European Pat. Off. . |
| A-05-310 580 | 11/1993 | Japan . |
| A-06-107 538 | 4/1994 | Japan . |

OTHER PUBLICATIONS

Joel Mindel et al. "*Therapeuric Review*" Jan. Feb. 1990, pp.268–290.

Hermann D. Schubert et al. "*Exogenous Na–Hyaluronate in The Anterior Chamber Of The Owl Monkey And Its Effect On The Intraocular Pressure*", Apr. 1, 1984. pp. 137–152.

*Primary Examiner*—Zohreh Fay
*Attorney, Agent, or Firm*—McDermott, Will & Emery

[57] ABSTRACT

The present invention relates to an ophthalmic formulation, for use in eye surgery, comprising sodium hyaluronate, citrate, at least one antioxidant tolerated by the intraocular tissues and a phosphate buffer.

10 Claims, 2 Drawing Sheets

SODIUM HYALURONATE BASED OPHTHALMIC FORMULATION FOR USE IN EYE SURGERY

FIELD OF THE INVENTION

The present invention relates to an ophthalmic formulation, for use in eye surgery, comprising sodium hyaluronate, citrate, at least one antioxidant tolerated by the intraocular tissues and a phosphate buffer.

Particularly, the present invention will comprise sodium hyaluronate having molecular weight from 1,000,000 to 2,000,000 Daltons.

PRIOR ART

Sodium hyaluronate (NaHA) based solutions have already been used for some time in eye surgery.

Loss of corneal endothelial cells and elevation in intraocular pressure (P.I.O.) after cataract operations with or without implantation of intraocular lenses are two negative consequences of such operations. Particularly, loss of endothelial cells can cause serious problems since such cells do not regenerate.

As for causes of elevation in pressure and mechanisms related with the loss of endothelial cells, various hypothesis have been suggested (Liesegang, T. J., 1990, Survey Ophtalmol., 34, 268–293). Nevertheless, the problems are still unsolved and the discovery of novel viscoelastic products able to limit or eliminate injuries resulting from operation, is still of great interest for safety of eye surgery. Sodium hyaluronate of pharmaceutical purity has already been used in production of solutions for eye surgery and various methods of preparation of the polymer having molecular weight from about 150,000 to about 6,000,000 Daltons are likewise known (U.S. Pat. No. 4,141,973). Products which are at present in use have determined a great progress in eye surgery, for example in cataract operation.

Particularly, the product commercially known as Healon® trade-mark, by Kabi Pharmacia, containing 1% of hyaluronic acid having molecular weight of about 4,000,000 Daltons and a viscosity of about 200 cps which appears to be the most used product in the world, has ideal rheologic characteristics for eye microviscosurgery. Nevertheless, it presents the serious inconvenience that it has to be removed from the eye after operation. As a matter of fact, Healon® which remains in the eye causes pathologic elevation in P.I.O. (Shubert et al., 1984, Exp. Eye Res., 39, 137–152) and just a slight defence of endothelium.

Nevertheless, removal of Healon® from the eye performed by the surgeon after the operation is not likely to be complete and Healon® traces usually remain in the eye even after removal, with the result of evident consequences for the patient.

Phacoemulsification has recently become the most used technique as for cataract operation. Advantages of such technique compared to techniques previously used can be summarized in a smaller incision, shorter time required for the operation and a more rapid rehabilitation of the patient. Nevertheless, this technique doesn't permit to cancel the postoperative elevation in P.I.O., in both cases in which Healon® or one of the other substances known in Literature are used as viscoelastic substances, and it might cause complications to the corneal endothelium, owing to manipulation performed by the surgeon in the anterior chamber of the patient's eye.

Injuries to the corneal endothelium caused by phacoemulsification have been related to mechanical trauma caused by surgical manipulation and by irrigation of the eye with salt solutions.

Therefore, it would be important to provide a novel composition able to eliminate the dangerous inconveniences which can result from small amounts of Healon® which remain in the eye, besides those which can result from inconveniences owing to mechanical removal of Healon® from the eye which has been operated upon, immediately after operation.

SUMMARY OF THE INVENTION

The author of the present invention surprisingly found an ophthalmic formulation, comprising hyaluronic acid, or a salt thereof, a citric acid salt, typically tri-sodium citrate, an antioxidant tolerated by the intraocular tissues and a phosphate buffer, which has such characteristics to reduce the toxic effects owing to the operation and which can be left "in situ" without causing any significant elevation in P.I.O.

Particularly, the present invention relates to a pharmaceutical formulation having a viscosity of 18,000–36,000 cps at 2 $sec^{-1}$ and at 25° C., and comprising hyaluronic acid having molecular weight of 1,000,000–2,000,000 Daltons and at the concentration of 1.5%–3.5% weight by volume, at least one antioxidant tolerated by the intraocular tissues, citrate at the concentration of 0.01%–0.05% weight by volume and phosphate buffer in order to maintain the formulation isotonic.

DETAILED DESCRIPTION OF THE INVENTION

Figure 1:
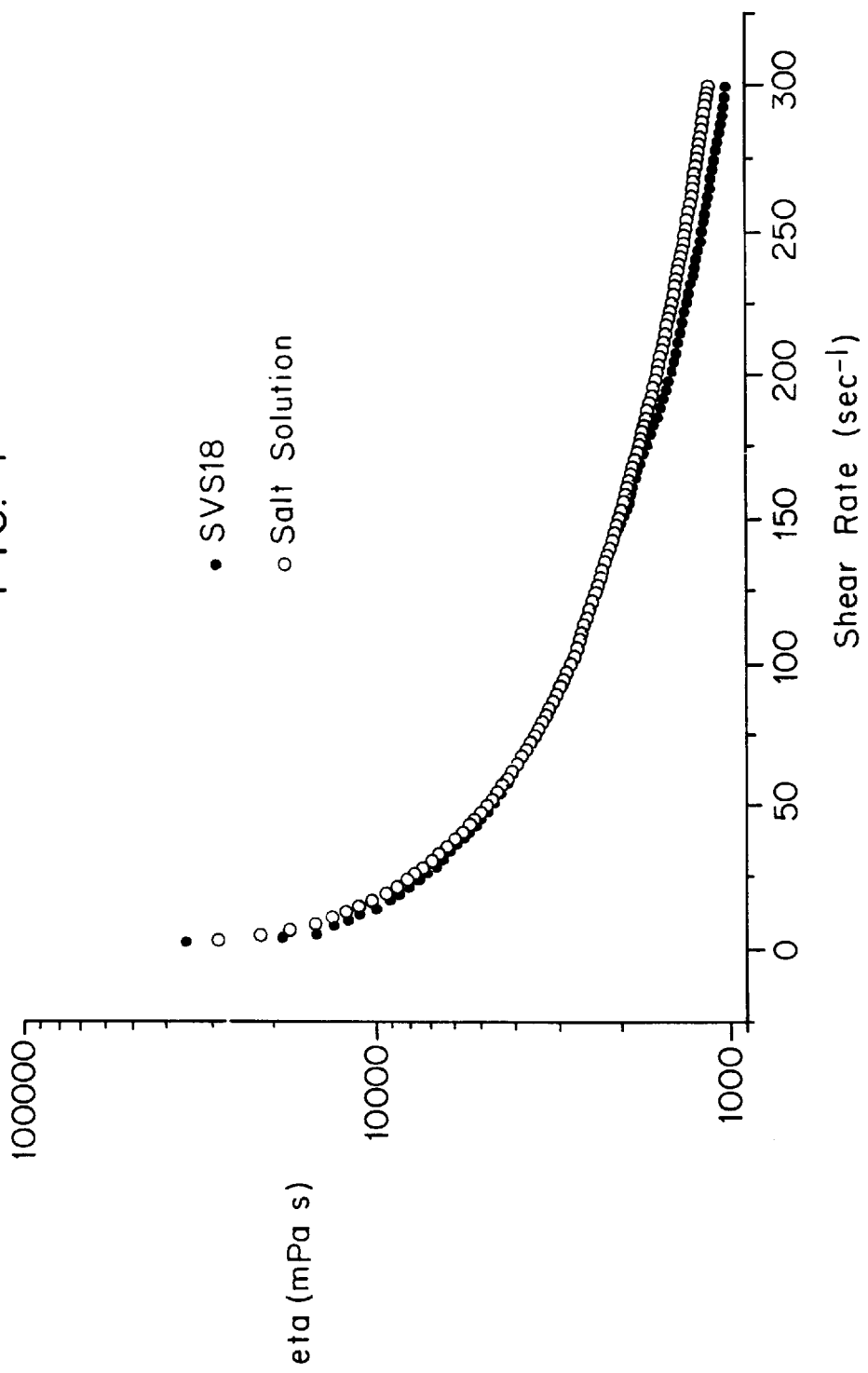
FIG. 1 shows a flow curve concerning the viscosity variation (eta) relative to the shear rate ($sec^{-1}$) for the viscoelastic and non-Newtonian solution SVS18 (GII) and the salt solution (GIII). Values of the shear rate ($sec^{-1}$) are reported on abscissa and values of the viscosity variation expressed by eta (mPa.s.) are reported on ordinate.

The present invention comprises a sodium hyaluronate solution in combination with a citric acid salt, typically tri-sodium citrate, at least one antioxidant tolerated by the intraocular tissues in isotonic salt solution buffered at neutral pH.

According to a typically embodiment of the present invention, the hyaluronic acid salt may be the only viscosity thickener included in the present formulations.

The method of preparation of the solution object of the present invention requires mixing of the components under aseptic conditions, by means of techniques and equipments usual for ophthalmic preparations.

The resulting formulation has a viscosity of 18,000–41,000 cps (cps=centipoises) at 2 $sec^{-1}$, at 25° C.

Extractive (e.g., from cock comb, umbilical cord, etc.) or fermentative (e.g., from Streptococcus, ect.) NaHA has a molecular weight of 1,000,000–2,000,000 Daltons and a concentration of 15–35 mg/ml, which produces a preparation having a viscosity of 18,000– 41,000 cps at 2 $sec^{-1}$ and at 25° C., preparation which maintains its own rheologic characteristics even in presence of substances such as sodium citrate, an antioxidant, e.g. sodium ascorbate and/or glucose, phosphate buffer and, if that is the case, sodium chloride, potassium chloride, magnesium chloride and calcium chloride. According to a preferred embodiment, the present formulations have a viscosity of 18,000 to 41,000 cps at a share rate of 2 sec$^{-1}$, at 25° C., and of 550 to 1,250 cps at a share rate of 300 sec$^{-1}$, at 25° C., corresponding to a viscosity versus share variation index (ratio of eta 1 sec$^{-1}$/eta 300 sec$^{-1}$) of about 33. In the present formulation, the citrate will be at the concentration of 0.01%–0.05%, preferably 0.03% weight by volume.

As antioxidant tolerated by the intraocular tissues, it will be possible to use at least one of the antioxidants selected from the group comprising glucose, ascorbate, sulphides, superoxide dismutase (SOD), cysteine and derivates thereof. Furthermore, other antioxidants, tolerated by the intraocular tissues, known in literature, can be used, e.g. hydrosoluble antioxidants, antioxidants which have at least one —SH or —CHO group, peptides and enzymes. Particularly, as antioxidant it will be possible to use sodium ascorbate at the concentration of 0.01%–1%, preferably 0.02% weight by wolume, and/or glucose at the concentration of 0.04%–4%, preferably 0.07% weight by volume.

The applicant has unexpectedly found that antioxidants significantly reduce hyaluronic acid degradation due to sonication following pharmacoemulsification.

Typically, the present formulations contain an ascorbic acid salt, such as sodium ascorbate, as the antioxidant, preferably in association with another antioxidant.

Typical formulations according to the present invention contain both ascorbate and glucose.

As for phosphate salts based buffer, this is added in an amount sufficient to produce a neutral isotonic aqueous solution (e.g. pH 7.0–7.4, preferably pH 7.2).

According to a particular embodiment, besides the elements mentioned above, the formulation according to the present invention may comprise an isotonic salt solution comprising sodium chloride, potassium chloride, magnesium chloride, calcium chloride and dibasic sodium phosphate.

Therefore, the formulation according to the present invention may have the following composition:

| | |
|---|---|
| NaHA (M.W. 1,000,000–2,000,000 Daltons); | 1.5–3.5% |
| Na$_3$citrate | 0.01–0.05% |
| Sodium ascorbate | 0.01–1.0% |
| glucose | 0.04–4.0% |
| Na$_2$HPO$_4$.12H$_2$O | 0.26–0.39% |
| NaCl | 0.54–0.81% |
| KCl | 0.15–0.23% |
| MgCl$_2$.6H$_2$O | 0.01–0.02% |
| CaCl$_2$.H$_2$O | 0.007–0.011% |
| water up to 100 ml.; pH 7.2–7.4 | |

According to further preferred embodiments, ascorbate concentrations are of 0.01–0.03%; glucose concentrations are of 0.04–1.00%; NaCl concentrations are of 0.60–0.70%.

According to a further preferred embodiment, the formulation according to the present invention may have the following composition:

| | |
|---|---|
| NaHA (M.W. 1,000,000–2,000,000 Daltons); | 2.5% |
| Na$_3$citrate | 0.03% |
| Sodium ascorbate | 0.02% |
| glucose | 0.07% |
| Na$_2$HPO$_4$.12H$_2$O | 0.32% |
| NaCl | 0.54–0.68% |
| KCl | 0.15–0.19% |
| MgCl$_2$.6H$_2$O | 0.01–0.014% |
| CaCl$_2$.H$_2$O | 0.007–0.009% |
| water up to 100 ml.; pH 7.2 | |

Unless otherwise stated, in the present text the % amounts of the components correspond to weight/volume %.

The aim of the present invention is also achieved using hyaluronic acid salts other than the sodium salt, as well as Na$^+$, K$^+$, Ca$^{++}$ and Mg$^{++}$ salts different from those hereinabove mentioned, preferred composition containing in addition to 1.5–3.5% weight/volume of a hyaluronic acid salt, the following amounts of ionic species and of glucose: Na$^+$ 100–220 mmo/l, and more preferably 100–150 mmol/l (not included that coming from NaHA); K$^+$ 20–30 mmol/l, typically about 25 mmol/l; Ca$^{++}$ 0.50–0.90 mmol/l, typically about 0.7 mmol/l; Mg$^{++}$ 0.40–1.00 mmol/l, typically about 0.7 mmol/l; Cl$^-$ 100–180 mmol/l, more preferably about 140–150 mmol/l; HPO$_4$=7.0–11.00 mmol/l, typically about 9 mmol/l; citrate 0.30–2.00 mmol/l, typically 0.4–1.2 mmol/l; ascorbate 0.50–55.00 mmol/l, typically 0.50–1.00 mmol/l; glucose 2.0–225.00 mmol/l, typically 2.2–5.0 mmol/l.

The formulation according to the present invention has been used in the ophthalmic surgery in general. Particularly, in the ophthalmic surgery of the anterior segment (cataract, glaucoma, corneal or conjunctival pathology, etc.) or of the posterior segment (vitreumectomy, detachment of retina, etc.) and it proved to be extremely efficient, particularly during cataract operation and more particularly during utilization of phacoemulsification.

The formulation according to the present invention appears to fulfil requirements of viscoelasticity and non-Newtonian behaviour necessary to the ophthalmic surgery, particularly to the cataract operation, either in presence or in absence of phacoemulsification. Furthermore, such formulation shows remarkable advantages when compared to the preparations on the market used in the eye surgery, that are Healon® (Kabi Pharmacia) or Viscoat® (Alcon):

i) a lower influence on P.I.O.;
  ii) it can be left "in situ" after the operation, instead of being removed; therefore, it avoids the remaining of residual traces, even after removal from the eye;
  iii) a lower inflammatory effect (phlogosis);
  iv) a lower loss of corneal endothelium cells, even when measured just 3 months after the operation.

Now, the present invention will be disclosed in the following example, according to a particular embodiment and compared to a solution known by the Prior Art.

The observation that the present formulations are endowed with good non-Newtonian properties, is in particular unexpected in view of the teaching of U.S. Pat. No. 5,106,615, with reports that amounts of NaCl above 0.01% by weight (i.e. above 1.75 mmoles/l) destroy the non-Newtonian behaviour of hyaluronate based solutions, and that Ca$^{++}$ and other bivalent cations are even more efficient, as well as data showing that 25 mmoles/l of NaCl abolish such non-Newtonian behaviour.

Viscoelasticity is a rheological property possessed by materials which are viscous, but also exhibit elastic deformation when stressed (Remington's Pharmaceutical Science, Mack Publishing Company, 18th Ed., pages 319–320), whereas non-Newtonian behaviour is a rheological property, possessed by materials the viscosity of which varies in a manner not proportional to the applied shear stress (McGraw Hill Dictionary of Scientific Technical Terms, pages 479, 1010, 1020, 1601). So the two aforementioned properties refer to different rheological aspects, which may be concurrently present in some materials, such as for instance in hyaluronate based solutions substantially free from salts.

EXAMPLE 1

Comparative Test for Phacoemulsification

The surprising efficacy of the formulation according to the present invention was examined in a clinical study with 60 patients with cataract, patients who were assigned to 3 groups (indicated as GI, GII and GIII) each of 20 members, operated by means of phacoemulsification technique described and standardized hereinafter:

- scleral incision (350 microns deep) parallel to the limbus (1–2 mm behind this one);
- preparation of the scleral tunnel by means of lancet;
- aperture of the anterior chamber (by means of 3.2 mm callipered (calibrated) blade with inclination <45°;
- input of the viscoelastic solution into the anterior chamber (total replacement of the aqueous humour);
- capsulorrhexis, hydrodissection and nucleodelineation;
- phacoemulsification (cross technique);
- aspiration of the masses and input of the viscoelastic solution into the capsular sac;
- implantation of 5 mm intracapsular eye lens;
- aspiration of the Healon® (GI), while the formulation according to the present invention (GII) and the solution of control (GIII) remain "in situ";
- apposition of a suture, if that is the case;

The average time of ultrasound used in the phacoemulsification is of 60 seconds ±15 seconds. The viscoelastic preparations used in this test were:

a) Healon®, whose composition is the following one:

| | |
|---|---|
| HA (M.W. 4,000,000 Daltons) | 1.0 g |
| NaCl | 0.85 g |
| $Na_2HPO_4.2H_2O$ | 0.028 g |
| $NaH_2PO_4.H_2O$ | 0.004 g |
| and water for injectable preparations up to 100 ml, for the GI; | | b) a formulation according to a particular embodiment of the present invention having the following composition (indicated as SVS 18):

| | |
|---|---|
| Hyaluronic acid (M.W. 1,350,000 Daltons); | 2.5 g |
| $Na_3$citrate | 0.031 g |
| Sodium ascorbate | 0.022 g |
| glucose | 0.070 g |
| $Na_2HPO_4.12H_2O$ | 0.322 g |
| NaCl | 0.678 g |
| KCl | 0.194 g |
| $MgCl_2.6H_2O$ | 0.014 g |
| $CaCl_2.H_2O$ | 0.009 g |
| water for injectable preparations up to 100 ml.; pH 7.2 for GII; and | | c) a preparation of a control salt solution containing:

| | |
|---|---|
| HA (M.W. 1,350,000 Daltons) | 2.5 g |
| NaCl | 0.850 g |
| $Na_2HPO_4.2H_2O$ | 0.322 g |
| $NaH_2PO_4.H_2O$ | 0.004 g |
| water for injectable preparations up to 100 ml, pH 7.2 for the GIII; | |

GI was constituted of 12 men and 8 women being the average age of 60 years (range 35–72), GII was constituted of 11 men and 9 women being the average age of 62 years (range 38–72) and GIII was constituted of 11 men and 9 women being the average age of 61 years (range 34–73).

All operations were performed by the same surgeon, who always used the same technique, the same amount of viscoelastic substance and who removed the Healon® after the operation, while he left "in situ" the formulation according to the present invention and the salt solution of control.

After the operation, all patients were treated with a subconjunctival injection of 6 mg of betamethasone and with a dexamethasone and tobramycin based collyrium.

The topic therapy was performed for 3 weeks every morning and it was associated with 1% tropicamide based collyrium.

Parameters which were considered in this study were: intra-ocular pressure (P.I.O.) evaluated by means of applanation tonometry the day before the operation and then after 6 hours, 12 hours, 1, 7, 30 and 60 days; it must be recalled to memory that physiologic value of intra-ocular pressure is <21 mmHg; the postoperative inflammation was valued after 1, 3, 7, 30 and 60 days after the operation and it was expressed by arbitrary units (0=absent, +=slight, ++=intermediate, +++=intense); number and morphology of endothelial cells were evaluated by Zeiss specular endothelial microscopy before the operation and after 2 months. Results are reported in Tables 1, 2 and 3, respectively. By observing such Tables 1, 2 and 3, it is possible to assert what follows:

i) the formulation according to the present invention (SVS 18 of GII) relative to the Healon® can be left "in situ" after the operation, which not only doesn't cause elevation in pressure (on the contrary, after 6 hours the group treated with Healon®, that is GI, has an average pressure of 21±7 mmHg against 18±6 mmHg of GII) (Table 1), but it also explains the lower incidence of postoperative phlogosis during the first day after the operation (Table 2);

ii) the formulation according to the present invention is the iscoelastic substance which permits the lower loss of endothelial cells (-7% two months after the operation), while the group wherein Healon® was used (GI) did undergo a loss of 11% during the same period of 2 months (Table 3);

TABLE 1

INTRA-OCULAR PRESSURE (mmHg)
mean value ± Standard Deviation

| PATIENTS | PRESSIONE TIME | | | | | | | |
|---|---|---|---|---|---|---|---|---|
| | 0 | 6 h | 12 h | 1 g | 3 g | 7 g | 30 g | 60 g |
| GI (HEALON*) | 14 ± 4 | 21 ± 7 | 19 ± 5 | 18 ± 3 | 18 ± 4 | 16 ± 2 | 18 ± 2 | 15 ± 4 |
| GII (SVS 18) | 15 ± 2 | 18 ± 6 | 18 ± 6 | 17 ± 4 | 16 ± 3 | 15 ± 2 | 15 ± 3 | 16 ± 4 |
| GIII (SALT SOLUTION) | 12 ± 5 | 18 ± 7 | 19 ± 6 | 19 ± 4 | 17 ± 5 | 18 ± 3 | 16 ± 4 | 15 ± 3 |

TABLE 2

OCULAR PHLOGOSIS
arbitrary unit (0 = absent; + = slight; ++ = intermediate; +++ = intense)

| PATIENTS | | DEGREE OF PHLOGOSIS TIME | | | | |
|---|---|---|---|---|---|---|
| | | 1 day | 3 days | 7 days | 30 days | 60 days |
| GI (HEALON*) | 0 | 0 | 0 | 0 | 12 | 20 | 20 |
| | + | 9 | 15 | 8 | 0 | 0 |
| | ++ | 11 | 5 | 0 | 0 | 0 |
| | +++ | 0 | 0 | 0 | 0 | 0 |
| GII (SVS 18) | 0 | 0 | 0 | 0 | 18 | 20 | 20 |
| | + | 14 | 16 | 2 | 0 | 0 |
| | ++ | 6 | 4 | 0 | 0 | 0 |
| | +++ | 0 | 0 | 0 | 0 | 0 |
| GIII (SALT SOLUTION) | 0 | 0 | 1 | 2 | 16 | 19 | 20 |
| | + | 11 | 12 | 4 | 1 | 0 |
| | ++ | 9 | 6 | 0 | 0 | 0 |
| | +++ | 0 | 0 | 0 | 0 | 0 |

TABLE 3

ENDOTHELIAL CELLS DENSITY
mean value ± Standard Deviation

| PATIENTS | PERIOD | |
|---|---|---|
| | PRE-OPERATIVE | 60 days |
| GI (HEALON*) | 2650 ± 450 | 2359 ± 425 |
| GII (SVS 18) | 2780 ± 333 | 2594 ± 370 |
| GIII (SALT SOLUTION) | 2690 ± 380 | 2448 ± 390 | iii) the difference on endothelial cells between the two GII and GIII groups treated with SVS 18 and with the control salt solution respectively, is a clear evidence of the favourable effect of the formulation according to the present invention comprising the citrate and at least one antioxidant (as for the present case, sodium ascorbate and glucose) with respect to the one wherein sodium hyaluronate at the same concentration and having the same molecular weight is in buffered salt solution, only (Table 3).

By observing FIG. 1, it can be noted that the SVS18 solution has a viscosity versus share rate variation index (ratio of eta 1 sec$^{-1}$/eta 300 sec$^{-1}$) of 33.6, while the same value is of 24.6 for the salt solution (GIII). The result is that the SVS18 has a viscosity versus share rate variation index of +27% with respect to the salt solution.

For the purpose of its utilization in ophthalmic surgery, in particular in cataract operation, the most important rheologic characteristic is the viscosity versus shear rate variation index, considered as ratio between two viscosity (low shear rate viscosity, non-moving fluid and high shear rate viscosity, fluid under mechanical stress).

The viscosity versus shear rate variation index is a measure of the versatility of a non-Newtonian substance, wherein the higher the index is, the more versatile the non-Newtonian fluid is from a rheologic point of view and therefore it will show a better behaviour during the operation.

The increase of +27% of the index, reported in FIG. 1, confirms the fact that the SVS18 solution has rheologic characteristics more suitable for the needs of the operation exactly because of its peculiar formulation, making it superior over the salt solution.

EXAMPLE 2

Effect of the Antioxidants on Sonicated Formulations

The effect of stabilization of the degradation of a sodium hyaluronate sonicated solution with a phacoemulsificator has been evaluated by means of addition of antioxidants.

Different formulations were prepared. The first one corresponded to the one reported in Example 1, but without antioxidants (neither glucose, nor ascorbate), while the other ones corresponded to the previous formulation, but comprising ascorbic acid at 0.02% as well as glucose 0.07% weight/volume.

Such solutions were sonicated for 5 minutes with a Alcon mod. Universal phacoemulsificator. The degradation of the sodium hyaluronate solution was monitored by means of viscosimetric measures performed before and after sonication with a BOHLIN VOR viscosimeter (Bohlin AG).

Figure 2:
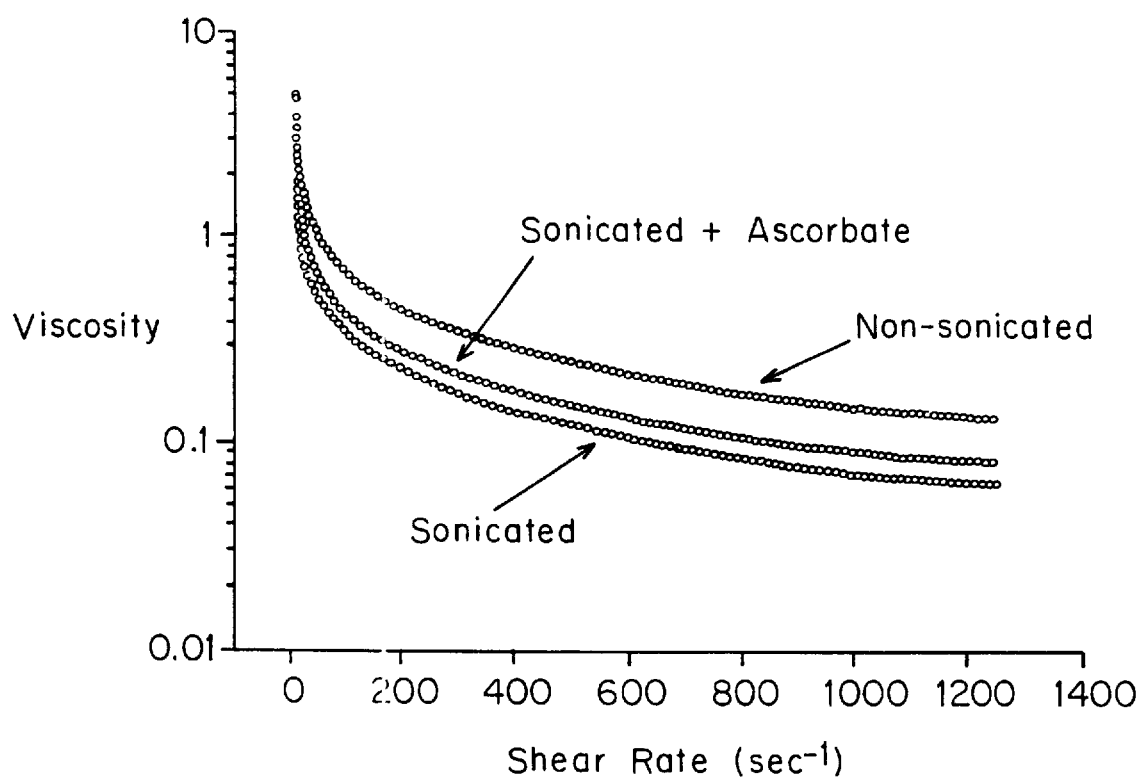
FIG. 2 shows a flow curve of a solution according to the present invention: a) non-sonicated, without antioxidant; b) sonicated, without antioxidant; and c) sonicated, but having sodium ascorbate as antioxidant. Values of the shear rate ($sec^{-1}$) are reported on abscissa and the viscosity (eta) is reported on ordinate.

The results which were obtained are shown in FIG. 2, wherein a flow curve of a solution according to the present invention a)non-sonicated, without antioxidant; b)sonicated, without antioxidant; and c)sonicated, but having sodium ascorbate as antioxidant, is reported. By observing the flow curves showed in FIG. 2, which were obtained for the formulation containing sodium ascorbate, a higher viscosity and a stabilization of about 20% relative to the sonicated solution without sodium ascorbate were observed.

Furthermore, the present invention relates to the use of an aqueous sodium hyaluronate solution, having molecular weight of 1,000,000–2,000,000 Daltons and a concentration of 1.5%–3.5% weight by volume in combination with 0.01%–0.05% weight by volume of citrate, and at least one antioxidant tolerated by the intraocular tissues and a phosphate buffer for the preparation of an ophthalmic formulation, where the obtained ophthalmic formulation has a viscosity of 18,000–41,000 cps at 2 sec$^{-1}$ at 25° C.

Furthermore, the present invention relates to a therapeutic method of ophthalmic surgery by means of utilization for the eye of a viscoelastic sodium hyaluronate based formulation according to the present invention.

Particularly, the present invention relates to a therapeutic method of ophthalmic surgery of the anterior segment (cataract, glaucoma, corneal or conjunctival pathology, etc.) or posterior segment (vitreumectomy, detachment of retina, etc.). More particularly, it relates to a method of cataract operation by means of phacoemulsification, of glaucoma operation by means of trabeculectomy, of corneal operation (keratoplasty), etc.

I claim:

1. An ultrasound-resistant ophthalmic formulation having a viscosity of 18,000–41,000 cps at 2 $sec^{-1}$ at 25° C., and of 550 to 1,250 cps at a shear rate of 300 $sec^{-1}$ at 25° C., comprising:
    (a) 1.5%–3.5% by volume of hyaluronic acid having a molecular weight of 1,000,000–2,000,000 Daltons or a salt thereof as a viscosity thickener,
    (b) an ascorbic acid salt tolerated by the intraocular tissues in association with at least a further antioxidant,
    (c) a citric acid salt, and
    (d) a phosphate buffer.

2. The formulation according to claim 1, wherein said ascorbic acid is sodium ascorbate.

3. The formulation according to claim 1, wherein said antioxidant is sodium ascorbate at a concentration of 0.01%–1.00 weight by volume.

4. The formulation according to claim 1, where said further antioxidant is selected from the group consisting of glucose, cysteine and derivatives thereof, sulphides, superoxide dismutase, hydrosoluble antioxidants, antioxidants having at least one —SH or —CHO group, peptides, enzymes, and mixtures thereof.

5. A method for using the formulation according to claim 1, comprising applying the formulation as a solution intraocularly during an eye surgery procedure involving phacoemulsification.

6. A therapeutic method for the treatment of eye diseases by means of an eye surgery treatment, comprising intraocularly applying to a subject in need of such treatment a therapeutically effective amount of an ophthalmic formulation according to claim 1.

7. The therapeutic method according to claim 6, which comprises leaving said ophthalmic formulation in situ after surgical treatment.

8. The therapeutic method according to claim 6, wherein said eye surgery treatment includes phacoemulsification.

9. The therapeutic method according to claim 6, which comprises the steps of
    (a) providing scleral incision parallel to the limbus;
    (b) preparing the scleral tunnel by means of lancet;
    (c) providing aperture of the anterior chamber by means of a 3.2 mm calibrated blade with inclination <45°;
    (d) inserting the ophthalmic formulation into the anterior chamber, providing total replacement of aqueous humor;
    (e) effecting capsulorrexix, hydrodissection and nucleodelineation;
    (f) effecting phacoemulsification by means of cross technique;
    (g) effecting masses aspiration and inserting the ophthalmic solution into the capsular sac;
    (h) implanting the intracapsular eye lens;
    (i) leaving the formulation in situ; and
    (j) suturing if necessary.

10. The therapeutic method according to claim 6, wherein phacoemulsification comprises an ultrasound treatment for an average time of 60 seconds ±15 seconds.

* * * * *